(12) United States Patent
Kiesele et al.

(10) Patent No.: US 6,251,244 B1
(45) Date of Patent: *Jun. 26, 2001

(54) ELECTROCHEMICAL MEASURING CELL FOR DETECTING HYDRIDE GASES

(75) Inventors: Herbert Kiesele; Frank Mett, both of Lübeck (DE)

(73) Assignee: Dräger Sicherheitstechnik GmbH, Lübeck (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/353,047

(22) Filed: Jul. 13, 1999

(30) Foreign Application Priority Data

Jul. 18, 1998 (DE) .............................. 198 32 395

(51) Int. Cl.⁷ .................................. G01N 27/404
(52) U.S. Cl. ...................... 204/415; 204/431; 204/432; 205/794.5; 205/775
(58) Field of Search ................... 204/415, 431, 204/432; 205/794.5

(56) References Cited

U.S. PATENT DOCUMENTS 4,571,292 * 2/1986 Liu et al. ............................ 204/415
5,128,018   7/1992 Kiesele .
5,316,648   5/1994 Kühn et al. .
5,997,706 * 12/1999 Kiesele et al. ...................... 204/415

FOREIGN PATENT DOCUMENTS 3923717   1/1991 (DE) .
0239190   9/1987 (EP) .
0400488  12/1990 (EP) .
WO93/10444  5/1993 (WO) .
WO96/33404 10/1996 (WO) .

* cited by examiner

Primary Examiner—T. Tung
(74) Attorney, Agent, or Firm—Walter Ottesen

(57) ABSTRACT

The invention is directed to an electrochemical measuring cell for detecting hydride gases, preferably arsine and phosphine. The measuring cell includes at least one working electrode (3) made of a catalytically inactive material and a reference electrode (4) in an electrolyte chamber (6) filled with an electrolyte containing sulphuric acid. The measuring cell is improved as to the cross sensitivity with respect to other toxic gases. The working electrode is configured as a carbon electrode (3) and an electrolyte additive of silver sulphate is provided in saturated solution in the electrode (9).

19 Claims, 1 Drawing Sheet

ELECTROCHEMICAL MEASURING CELL FOR DETECTING HYDRIDE GASES

FIELD OF THE INVENTION

The invention relates to an electrochemical measuring cell for detecting hydride gases and especially arsine and phosphine. The measuring cell includes at least one working electrode made of a catalytically inactive material and a reference electrode in an electrolyte chamber filled with an electrolyte. The electrolyte chamber is closed off with respect to the gas to be detected by a diffusion membrane.

BACKGROUND OF THE INVENTION

An electrochemical measuring cell for detecting hydride gases such as phosphine and arsine is disclosed in U.S. Pat. No. 5,128,018. In this known measuring cell, a measuring or working electrode, a reference electrode and an auxiliary electrode are mounted in an electrolyte chamber of a measuring cell housing. The electrolyte chamber is closed off with a gas permeable diffusion membrane toward the ambient which contains the gas sample to be measured having the hydride gas to be detected. Sulphuric acid with catalyzing additives is used as an electrolyte.

Although the known measuring cell is characterized by a high sensitivity, cross sensitivities are present relative to a series of other gases. In specific applications, these cross sensitivities are especially disturbing or can lead to false alarms. In addition to phosphine and arsine, the known measuring cell also reacts to $NO_2$, $H_2$, $C_2H_2$, $SO_2$, $H_2O_2$ and $O_3$.

SUMMARY OF THE INVENTION

It is an object of the invention to provide an electrochemical measuring cell of the kind described above which is improved with respect to the cross sensitivity to other toxic gases.

The electrochemical measuring cell of the invention is for detecting hydride gases including arsine and phosphine. The electrochemical measuring cell includes: a housing having an opening directed toward the hydride gas to be detected and defining an electrolyte chamber; an electrolyte disposed in the electrolyte chamber; the electrolyte containing sulphuric acid and silver sulphate as an electrolyte additive; a working electrode configured as a carbon electrode; a reference electrode mounted in the electrolyte chamber so as to be in spaced relationship to the working electrode; and, a diffusion membrane permeable to the hydride gas mounted in the housing to define an interface between the hydride gas and the electrolyte chamber.

The advantage of the invention lies in the surprising realization that the selectivity of the detection of arsine and phosphine compared to other gases, such as $H_2$, $C_2H_2$ and $NO_2$, is significantly improved by a combination of a working electrode made of carbon with an electrolyte containing sulphuric acid to which silver sulphate is added as an electrolyte additive. Phosphoric acid can also be used as an electrolyte as an alternative to sulphuric acid with the phosphoric acid containing silver phosphate as an electrolyte additive.

The electrochemical reaction within the measuring cell takes place in such a manner that the phosphine or arsine to be detected reacts selectively with the electrolyte additive within the electrolyte chamber and the reaction product is then detected on the working electrode. By utilizing a working electrode made of carbon, a measuring cell of this kind supplies no or a very slight measuring signal in the presence of toxic gases such as $NO_2$ and $SO_2$. An electrochemical measuring cell, which contains sulphuric acid as an electrolyte and silver sulphate as electrolyte additive is distinguished by a high sensitivity and short response time with respect to the detection of arsine and phosphine.

The measuring cell according to the invention can be configured as a two-electrode measuring cell or also as a three-electrode measuring cell having an additional auxiliary electrode. The electrodes are then connected to a potentiostat as known per se.

It is especially purposeful to use, as an electrolyte, a mixture of phosphoric acid and sulphuric acid with silver phosphate as an electrolyte additive.

It is advantageous to use the electrolyte additive in saturated solution. Measuring cells configured in this manner have an especially high long-term stability. A saturated solution of the electrolyte additive is advantageously achieved in that the electrolyte additive is present as a solid phase in the electrolyte chamber. In this way, consumed electrolyte additive can be continuously replaced by the solid phase. The solid phase can be, for example, a sediment or a precipitate.

The carbon electrode is purposefully configured as a thick film electrode. The carbon electrode can be cut from a plate-shaped material. The preferred thickness of the carbon electrode lies between 1 to 2 mm. Carbon paper, glassy carbon or porous glassy carbon can also be used as a material for the working electrode.

A sintered carbon electrode has been shown to be especially advantageous and comprises a mixture of carbon and PTFE (polytetrafluoroethylene). An electrode of this kind can be applied to the porous PTFE diffusion membrane with a casting process or with a screen printing process.

The thickness of the sintered carbon electrode preferably lies between 100 $\mu$m and 1,000 $\mu$m.

A carbon electrode made of a sintered mixture of carbon and gold provides especially good results.

The reference electrode and the auxiliary electrode can be made of gold, platinum, iridium, silver, ruthenium, rhodium or palladium.

BRIEF DESCRIPTION OF THE DRAWINGS

The invention will now be described with reference to the single figure of the drawing (FIG. 1) which shows a longitudinal section view of the electrochemical measuring cell according to an embodiment of the invention.

DESCRIPTION OF THE PREFERRED EMBODIMENTS OF THE INVENTION

Figure 1:
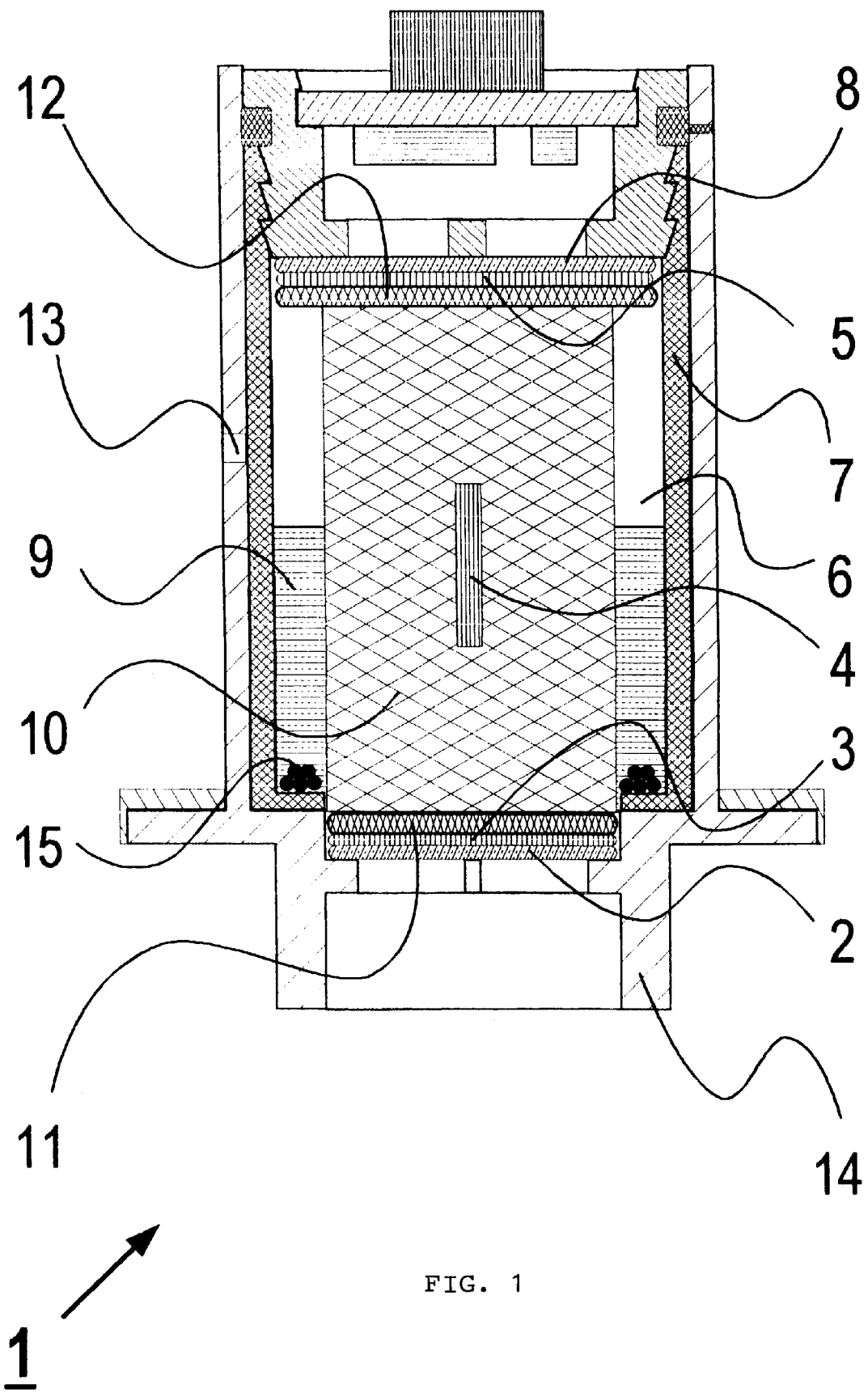

FIG. 1 shows an electrochemical measuring cell having a porous PTFE diffusion membrane 2, a carbon electrode 3 as a working electrode, a reference electrode 4 made of gold and an auxiliary electrode 5 likewise made of gold. The working electrode 3 is made of a sintered mixture of carbon and PTFE. The electrodes 3, 4 and 5 are mounted in an electrolyte chamber 6 of a measuring cell housing 7.

A porous PTFE support membrane 8 is used as an electrode carrier for the auxiliary electrode 5. The electrolyte 9 is 4M sulphuric acid having an electrolyte additive of silver sulphate in a saturated solution. The saturated solution is obtained by a solid phase 15 of silver sulphate. Consumed silver sulphate can, in this way, be continuously replaced by the solid phase 15. The saturated solution adjusts automatically when a solid phase of silver sulphate is present in the electrolyte.

Within the electrolyte chamber 6, the electrolyte 9 is absorbed by a porous glass body 10 which holds the reference electrode 4 at its center and establishes the electrolytic connection between the electrodes (3, 5) via two nonwoven fabrics (11, 12). The carbon electrode 3 is applied in the casting method to the diffusion membrane 2 and thereafter sintered. The thickness of the carbon electrode 3 is 200 µm. Furthermore, the carbon electrode 3 is pressed against the diffusion membrane 2 by the nonwoven fabric 11.

The measuring cell housing 7 is comprised of porous PTFE and a pressure compensation between the electrolyte chamber 6 and the ambient is established by the breakthrough 13. The electrodes (3, 4, 5) are connected to a potentiostat (not shown) in a manner known per se. The gas sample, which contains the phosphine or arsine to be detected, reaches the carbon electrode 3 via the connection 14 and the diffusion membrane 2.

With the measuring cell of the invention, concentrations of phosphine and arsine can be detected in a concentration range below 50 ppb.

It is understood that the foregoing description is that of the preferred embodiments of the invention and that various changes and modifications may be made thereto without departing from the spirit and scope of the invention as defined in the appended claims.

What is claimed is:

1. An electrochemical measuring cell for detecting hydride gases including arsine and phosphine, the electrochemical measuring cell comprising:
   a housing having an opening directed toward the hydride gas to be detected and defining an electrolyte chamber;
   an electrolyte disposed in said electrolyte chamber;
   said electrolyte containing sulphuric acid and silver sulphate as an electrolyte additive;
   a carbon working electrode;
   a reference electrode mounted in said electrolyte chamber so as to be in spaced relationship to said carbon working electrode; and,
   a diffusion membrane permeable to said hydride gas mounted in said housing to define an interface between said hydride gas and said electrolyte chamber.

2. The electrochemical measuring cell of claim 1, wherein said electrolyte additive is contained in said electrolyte in saturated solution.

3. The electrochemical measuring cell of claim 1, further comprising a solid phase in said electrolyte chamber and said solid phase comprising said electrolyte additive.

4. The electrochemical measuring cell of claim 1, wherein said carbon working electrode is configured as a carbon thick film electrode.

5. The electrochemical measuring cell of claim 1, wherein said carbon working electrode is configured as a carbon/PTFE sinter electrode applied to said diffusion membrane.

6. The electrochemical measuring cell of claim 5, wherein said carbon/PTFE sinter electrode has a thickness of between 100 µm and 1000 µm.

7. The electrochemical measuring cell of claim 1, wherein said carbon working electrode is configured as a porous carbon disc.

8. The electrochemical measuring cell of claim 1, wherein said carbon working electrode comprises a sintered mixture of carbon and gold.

9. The electrochemical measuring cell of claim 1, wherein said carbon working electrode lies against said diffusion membrane.

10. An electrochemical measuring cell for detecting hydride gases including arsine and phosphine, the electrochemical measuring cell comprising:
    a housing having an opening directed toward the hydride gas to be detected and defining an electrolyte chamber;
    an electrolyte disposed in said electrolyte chamber;
    said electrolyte containing phosphoric acid and a silver phosphate as an electrolyte additive;
    a carbon working electrode;
    a reference electrode mounted in said electrolyte chamber so as to be in spaced relationship to said carbon working electrode; and,
    a gas-permeable membrane mounted in said housing to define an interface between said hydride gas and said electrolyte chamber.

11. The electrochemical measuring cell of claim 10, wherein sulphuric acid is added to said electrolyte.

12. The electrochemical measuring cell of claim 10, wherein said electrolyte additive is contained in said electrolyte in saturated solution.

13. The electrochemical measuring cell of claim 10, further comprising a solid phase in said electrolyte chamber and said solid phase comprising said electrolyte additive.

14. The electrochemical measuring cell of claim 10, wherein said carbon working electrode is configured as a carbon thick film electrode.

15. The electrochemical measuring cell of claim 10, wherein said carbon working electrode is configured as a carbon/PTFE sinter electrode applied to said diffusion membrane.

16. The electrochemical measuring cell of claim 15, wherein said carbon/PTFE sinter electrode has a thickness of between 100 µm and 1000 µm.

17. The electrochemical measuring cell of claim 10 wherein said carbon working electrode is configured as a porous carbon disc.

18. The electrochemical measuring cell of claim 10, wherein said carbon working electrode comprises a sintered mixture of carbon and gold.

19. The electrochemical measuring cell of claim 10, wherein said carbon working electrode lies against said diffusion membrane.

* * * * *